United States Patent [19]

Goetz

[11] Patent Number: 5,063,118

[45] Date of Patent: * Nov. 5, 1991

[54] ABRASIVE DENTAL STRIP

[75] Inventor: Roland Goetz, Winterthur, Switzerland

[73] Assignee: Sulzer Brothers Limited, Winterthur, Switzerland

[*] Notice: The portion of the term of this patent subsequent to Oct. 29, 2008 has been disclaimed.

[21] Appl. No.: 389,753

[22] Filed: Aug. 4, 1989

[30] Foreign Application Priority Data

Aug. 9, 1988 [CH] Switzerland .......................... 3006/88

[51] Int. Cl.$^5$ ............................................. C22C 32/00
[52] U.S. Cl. ..................................... 428/614; 428/606
[58] Field of Search .............................. 428/614, 606

[56] References Cited

U.S. PATENT DOCUMENTS 4,853,182 8/1989 Cornie et al. ........................ 420/590
4,865,806 9/1989 Skibo et al. .......................... 420/590

FOREIGN PATENT DOCUMENTS 0002785 7/1979 European Pat. Off. .
3533534 4/1987 Fed. Rep. of Germany .

Primary Examiner—Richard O. Dean
Assistant Examiner—David W. Schumaker
Attorney, Agent, or Firm—Kenyon & Kenyon

[57] ABSTRACT

The abrasive dental strip for teeth and teeth fillings is formed of a foil-like metal strips solidified from a melt and containing a homogeneous metal matrix in which hard particles such as zeta-chromium boride particles are fixed. The strip is easy to manufacture and provides increased protection against loosening of the hard particles from the strip during use.

17 Claims, No Drawings

ABRASIVE DENTAL STRIP

This invention relates to a metal abrasive dental strip. More particularly, this invention relates to a metal foil-like abrasive dental body for teeth and fillings.

As is known, various types of abrasive strips have been commercially known as finishing strips and polishing strips. Generally, the strips have been made of rolled strips of ordinary steel electrolytically coated on both sides with nickel. In addition, hard particles such as aluminum oxide (corundum) have been embedded in the nickel layer on one side and held by an additional electrolytically deposited nickel layer. The total thickness of such multi-layer strips is about 0.1 millimeter. Further, such strips have been offered for sale in various widths of from a few millimeters as well as in lengths of, for example, 15 centimeters.

Because of the rolling of the steel strip, the subsequent coating and the incorporation of hard particles into one of the nickel layers, the manufacturing of the strips has been relatively time consuming and expensive even though the resulting strips are generally made as disposable products in dental practice.

Furthermore, it has been found that the hard particles which have been fixed in the above noted matter can come loose from the nickel matrix relatively easily. Thus, not only do the strips have a short useful life but also the loose particles may become lodged between the teeth of a user.

As is also known, European Patent Application 0002785 describes a method of making strips of amorphous metal containing embedded particles of abrasive material. The method of making such strips involves forcing molten metal or a glass forming alloy containing admixed particulate matter onto the surface of a moving chill body under pressure through a slotted nozzle located in closed proximity to the surface of the chill body. As described, the strip product has utility as an abrasive grinding tape particularly for use in numerically controlled grinding machines.

Accordingly, it is an object of the invention to simplify the manufacture of a metal abrasive dental strip.

It is another object of the invention to improve the anchoring of hard particles in a matrix of an abrasive dental strip.

It is another object of the invention to provide a dental abrasive strip of relatively thin thickness.

It is another object of the invention to improve the flexibility of metal abrasive dental strips.

Briefly, the invention provides a metal foil-like abrasive dental strip for teeth and teeth fillings having a maximum thickness of one millimeter and having a metal matrix solidified from a melt of the metal with hard particles fixed in the matrix on one side.

The strip may be manufactured in accordance with the known metal-spinning matrix such as described in European Patent Application 0002785. In the case of the metal matrix, good results have been obtained by alloys which at least contain at least one element from group VIIIA, at least one element from groups IVA, VA or VIA and at least one of the elements boron, carbon, nitrogen, oxygen, silicon or phosphorus. The hard particles may be metal borides, carbides, nitrides, oxides, phosphides, silicides or diamond.

Alternatively, the hard particles can be in the form of granular material incorporated into the molten metal matrix in the melt-spinning plant, as described e.g. in European Patent Application 0002785. When the strip solidifies, the hard particles collect at one side of the exposed surface.

It has been found particularly advantageous, however, if the hard particles are in the form of primary segregations from the melt. The manufacture of a strip of this kind may be as described in U.S. patent application Ser. No. 301,623, filed Jan. 25, 1989.

The strips can be manufactured in thicknesses of 20 to 250 $\mu$m, measured between the smooth underside and the projecting tips of the hard particles on the rough surface. The resulting roughness, measured as smoothing depths $R_p$ (DIN 4762/1 or ISO 4287/1) are approximately between 2 and 100 $\mu$m.

Since relatively wide strips (e.g. 10 centimeters or more) can be manufactured by the melting-spinning process, the abrasive strip is also suitable as a polishing and/or cutting disc for grinding and polishing teeth and teeth fillings and for grinding prosthesis molds in the tooth-prosthesis industry. Hitherto, discs of the aforementioned kind and e.g. 8 to 15 millimeters in diameter have been made of plastics or plastics-coated fabric or papers covered with hard particles with the hard particles held on the substrate by adhesives.

For reasons of mechanical strength, the substrate needs to have a certain minimum thickness although this reduces the flexibility of the disc. On the other hand, flexibility is very important when grinding irregular contours.

As already mentioned, the abrasive metal strip can be made very thin, e.g. down to 20 $\mu$m. Discs which are made from such strips are therefore very flexible. In spite of the increased flexibility, the adhesion of the "abrasive" particles embedded in the metal matrix is better than in prior-art abrasive or cutting discs.

Various strips were manufactured by the process described in the above-noted U.S. patent application. In all examples, the following "parameters" were kept constant:

Composition of initial alloy (in % by weight): 60 Ni; 13 Cr; 4 Fe; 8 Si; 14B;

Remelting of initial alloy in 4 minutes;

Subsequent holding of re-molten initial alloy at 1060° C. for 1 minute;

Manufacture of strip by the melt-spinning process using a Cu-Cr alloy roll;

Thickness of strip; 50 $\mu$m;

Zeta chromium boride segregations as hard particles.

In order to vary the size of the hard particles and consequently vary the roughness, changes were made in the ingot mold in which the initial alloy was cast and solidified, and the speed of rotation of the CuCr alloy roll.

EXAMPLE 1

The initial alloy was poured into a steel ingot mold coated with zirconium oxide ($ZrO_2$). The speed of the roll was 1050 rpm. The resulting roughness, measured as a smoothing depth $R_p$ to DIN 4762/1 or ISO 4287/1, was 80 $\mu$m.

EXAMPLE 2

The initial alloy was poured into a non-coated steel ingot mold. The speed of the roll was 1200 rpm, and the resulting smooth depth $R_p$ was 30 $\mu$m.

EXAMPLE 3

The initial alloy was poured into the same non-coated steel ingot mold as in Example 2 but the speed of the roll was only 1000 rpm. In this case, the resulting smoothing depth $R_p$ 132 was 5 μm.

EXAMPLE 4

Discs having an outer diameter of 5 of 12 millimeters were cut out, e.g. by punching or electro-erosion, from a metal strip manufactured as per any of Examples 1 to 3. A concentric hole was formed in their center, suitable for commercial clamping holders or screw holders for polishing or cutting discs.

The resulting polishing discs had a thickness of 40 to 60 μm and roughness with a smoothing depth $R_p$ of e.g. 10 to 40 μm. Other discs of the same kind had a thickness of 80 to 100 μm, e.g. with a roughness of 80 μm measured as a resultant smoothing depth $R_p$.

A metal foil-like abrasive dental body can be produced in accordance with the above and formed into a strip or formed into discs, for example by cutting out of a larger strip. For example, discs have a diameter of from 8 to 15 millimeters may be formed out of strips of somewhat larger width.

The hard particles which are disposed on one side of the metal matrix of the metal body are preferably formed as primary segregations from the metal melt. Further, at least 50% of these hard particles have a skeletal crystal shape with a length to width ratio of at least 5. In some cases, at least 70% of the hard particles are so shaped.

The hard particles also form a rough structure on the body with projecting peaks wherein at least 80% of the peaks contain hard particles. Further, the hard particles projecting from the metal matrix are embedded in the matrix to at least 50% of the length thereof.

The invention thus provides a metal abrasive dental strip of relatively thin thickness. As such, the dental strip can be readily manipulated to perform and abrading function between teeth and teeth fillings. In this respect, the foil is very flexible.

The invention further provides a metal abrasive dental strip wherein hard particles on one surface of the strip are firmly embedded and are precluded from becoming loose during use.

What is claimed is:

1. A metal foil-like abrasive dental strip for teeth and fillings having a maximum thickness of one millimeter and having a metal matrix solidified from a melt of the metal with hard particles having skeletal crystal shapes fixed in said matrix on one side.

2. A metal strip as set forth in claim 1 wherein said metal matrix contains at least one metal selected from the group consisting of a metal from group VIIIA, at least one metal from one of groups IVA, VA and VIA and at least one of boron, carbon, nitrogen, oxygen, silicon and phosphorus.

3. A metal strip as set forth in claim 2 wherein said hard particles are selected from the group consisting of metal boride, -carbide, -nitride, -oxide, -phosphides and silicides and diamond.

4. A metal strip as set forth in claim 1 wherein said hard particles are primary segregations from the metal melt.

5. A metal strip as set forth in claim 4 wherein at least 50% of said hard particles have a skeletal crystal shape with a length to width ratio of at least 5.

6. A metal strip as set forth in claim 5 wherein at least 70% of said hard particles have a skeletal crystal shape with a length to width ratio of at least 5.

7. A metal strip as set forth in claim 5 wherein said hard particles form a rough structure on said one side having projecting peaks with at least 80% of said peaks containing said hard particles.

8. A metal strip as set forth in claim 7 wherein said hard particles projecting from said side are embedded in said matrix to at least 50% of the length thereof.

9. A metal foil-like abrasive dental body having a metal matrix and a plurality of hard particles fixed in said matrix and projecting from one side of said surface with a roughness of from 2 to 100 μm, said body having a thickness of from 20 to 250 μm; and wherein at least 50% of said hard particles having a skeletal crystal shape with a length to width ratio of at least 5.

10. A metal body as set forth in claim 9 wherein said hard particles projecting from said side are embedded in said matrix to at least 50% of the length thereof.

11. A metal body as set forth in claim 9 which is in the form of a strip.

12. A metal body as set forth in claim 9 which is in the form of a disc having a diameter of from 8 to 15 millimeters.

13. A metal body as set forth in claim 9 having a thickness of 50 μm.

14. A metal body as set forth in claim 13 wherein said hard particles are zeta chromium boride segregations.

15. A metal body as set forth in claim 14 wherein said matrix is made of 60 Ni 13 Cr 4 Fe 8 Si 14 B.

16. A metal body as set forth in claim 9 in the form of a disc having a thickness of from 40 to 60 μm and a roughness with a smoothing depth of from 10 to 40 μm.

17. A metal body as set forth in claim 9 in the form of a disc having a thickness of from 80 to 100 μm and a roughness with a smoothing depth of 80 μm.

* * * * *